United States Patent
Monson et al.

(10) Patent No.: US 10,959,659 B2
(45) Date of Patent: *Mar. 30, 2021

(54) INCONTINENCE DETECTION SYSTEM

(71) Applicant: Hill-Rom Services, Inc, Batesville, IN (US)

(72) Inventors: Gavin M. Monson, Oxford, OH (US);
Marwan Nusair, Cincinnati, OH (US);
Joseph T. Canter, Harrison, OH (US);
John D. Christie, Batesville, IN (US);
Dan Tallent, Hope, IN (US); James D. Voll, Columbus, IN (US); Bryan Weidman, Columbus, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/398,457

(22) Filed: Apr. 30, 2019

(65) Prior Publication Data

US 2019/0254583 A1 Aug. 22, 2019

Related U.S. Application Data

(62) Division of application No. 15/968,029, filed on May 1, 2018, now Pat. No. 10,349,881.

(Continued)

(51) Int. Cl.
*G07C 5/08* (2006.01)
*A61B 5/20* (2006.01)
(Continued)

(52) U.S. Cl.
CPC .............. *A61B 5/202* (2013.01); *A61B 5/002* (2013.01); *A61B 5/6808* (2013.01);
(Continued)

(58) Field of Classification Search
CPC ........ A61B 5/202; A61B 5/68; H01Q 1/2208; G06K 7/10356; A61F 13/42; G08B 21/20
See application file for complete search history.

(56) References Cited

U.S. PATENT DOCUMENTS

| 5,537,095 A | 7/1996 | Dick et al. |
|---|---|---|
| 6,340,932 B1 | 1/2002 | Rodgers et al. |

(Continued)

FOREIGN PATENT DOCUMENTS

| EP | 3451235 A1 | 3/2019 |
|---|---|---|
| EP | 3451235 A2 | 6/2019 |
| WO | 2017087452 A1 | 5/2017 |

OTHER PUBLICATIONS

U.S. Appl. No. 62/551,565, filed Aug. 29, 2017; Ryan S. Severns et al.

(Continued)

*Primary Examiner* — Hongmin Fan
(74) *Attorney, Agent, or Firm* — Barnes & Thornburg LLP

(57) ABSTRACT

A system for detecting an incontinence event includes a pad which is deployable on a mattress and which, as deployed, has a first conductor and a second conductor and in which the first conductor and the second conductor are not in electrical communication with each other. The system also incudes an RFID reader subsystem having a processor and an array of two or more spatially distributed antennas. The system is adapted to A) command transmission of energy from the antenna array at a variety of powers and at various frequencies, B) monitor the antenna array for a return signal resulting from the spatially and temporally varying transmission, and C) communicate a WET or DRY status to a destination. The WET or DRY status depends on a moisture status indicator of the return signal.

19 Claims, 12 Drawing Sheets

Related U.S. Application Data

(60) Provisional application No. 62/638,478, filed on Mar. 5, 2018, provisional application No. 62/633,243, filed on Feb. 21, 2018.

(51) Int. Cl.

| | | |
|---|---|---|
| *G08B 21/20* | (2006.01) | |
| *G06K 7/10* | (2006.01) | |
| *A61B 5/00* | (2006.01) | |
| *A61B 90/98* | (2016.01) | |
| *A61F 13/42* | (2006.01) | |
| *H01H 35/18* | (2006.01) | |
| *A61F 13/15* | (2006.01) | |

(52) U.S. Cl.
CPC ............ *A61B 5/6892* (2013.01); *A61B 5/742* (2013.01); *A61B 90/98* (2016.02); *A61F 13/42* (2013.01); *G06K 7/10366* (2013.01); *G08B 21/20* (2013.01); *H01H 35/18* (2013.01); *A61B 5/0022* (2013.01); *A61B 5/207* (2013.01); *A61B 5/7465* (2013.01); *A61B 2503/08* (2013.01); *A61B 2560/0468* (2013.01); *A61B 2562/164* (2013.01); *A61F 2013/15154* (2013.01); *A61F 2013/424* (2013.01)

(56) References Cited

U.S. PATENT DOCUMENTS

| | | | |
|---|---|---|---|
| 6,552,661 B1 | 4/2003 | Lastinger et al. | |
| 6,933,849 B2 | 8/2005 | Sawyer | |
| 6,982,646 B2 | 1/2006 | Rodgers et al. | |
| 7,055,754 B2 | 6/2006 | Forster | |
| 7,336,243 B2 | 2/2008 | Jo et al. | |
| 7,501,955 B2 | 3/2009 | Forster et al. | |
| 7,551,089 B2 | 6/2009 | Sawyer | |
| 7,650,636 B2 | 1/2010 | Forster et al. | |
| 7,834,765 B2 | 11/2010 | Sawyer | |
| 7,934,766 B2 | 5/2011 | Boczek et al. | |
| 8,279,069 B2 | 10/2012 | Sawyer | |
| 8,742,929 B2 | 6/2014 | Sawyer | |
| 8,840,013 B2 | 9/2014 | Sawyer | |
| 8,866,615 B2 | 10/2014 | Sawyer | |
| 8,896,449 B2 | 11/2014 | Sawyer | |
| 8,947,236 B2 | 2/2015 | Forster | |
| 9,396,369 B1* | 7/2016 | Whitehurst | G06K 19/07798 |
| 9,649,230 B1 | 5/2017 | Li | |
| 2003/0141962 A1 | 7/2003 | Barrink | |
| 2007/0241904 A1 | 10/2007 | Ozaki et al. | |
| 2008/0258876 A1* | 10/2008 | Overhultz | G06K 7/10336 340/10.2 |
| 2009/0017173 A1 | 1/2009 | Forster | |
| 2009/0189828 A1 | 7/2009 | Shmulevich et al. | |
| 2009/0195361 A1* | 8/2009 | Smith | H04B 5/02 340/10.1 |
| 2011/0249760 A1 | 10/2011 | Chrisikos et al. | |
| 2012/0075072 A1* | 3/2012 | Pappu | H04B 5/0062 340/10.1 |
| 2013/0113610 A1 | 5/2013 | Carrender et al. | |
| 2014/0276504 A1 | 9/2014 | Heil et al. | |
| 2015/0126216 A1 | 5/2015 | Mullins | |
| 2016/0374626 A1 | 12/2016 | Heil et al. | |
| 2017/0065464 A1 | 3/2017 | Heil et al. | |
| 2017/0098044 A1 | 4/2017 | Lai et al. | |
| 2017/0116444 A1 | 4/2017 | Karmakar et al. | |
| 2017/0243032 A1* | 8/2017 | Pesavento | G06K 7/10297 |
| 2017/0246063 A1* | 8/2017 | Monson | G16H 40/20 |
| 2018/0116878 A1* | 5/2018 | MacNaughton | A61F 13/42 |
| 2018/0325743 A1* | 11/2018 | Ho | A61B 5/6808 |

OTHER PUBLICATIONS

Adaptive and Probabilistic Power Control Algorithms for FRID Reader Networks; Kainan Cha, Anil Ramachandran, and Sarangapani Jagannathan; Department of Electrical and Computer Engineering, University of Missouri-Rolla, Rolla, Missouri; International Journal of Distributed Sensor Networks, 347-368, 2008; Copyright © Taylor & Francis Group, LLC; ISSN: 1550-1329 pring / 1550-1477 online; DOI: 10.1080/15501320701344107.

An Adaptive Power Control Algorithm in FRID Systems; X.Y. Huang, X.B. Zhu, K.L. Xu and J.H. Wu; Advanced Materials Research (/AMR) (vols. 1049-1050); https://www.scientific.net/AMR.1049-1050.1726.

European Search Report for EP Application 19157522.4; dated Jul. 15, 2019; Place of Search—Berlin; Date of Completion of Search—Jun. 28, 2019.

Extended European Search Report for European Patent Application No. 20159857.0 dated Jul. 2, 2020 (10 pages).

\* cited by examiner

| Transmission Number | Antenna Pair | Power (mW) | Frequency | Transmission Number | Antenna Pair | Power (mW) | Frequency |
|---|---|---|---|---|---|---|---|
| 1 | 1 | 1000 | f1 | 49 | 1 | 500 | f49 |
| 2 | 2 | 750 | f2 | 50 | 2 | 1000 | f50 |
| 3 | 3 | 500 | f3 | 51 | 3 | 750 | f1 |
| 4 | 4 | 1000 | f4 | 52 | 4 | 500 | f2 |
| 5 | 5 | 500 | f5 | 53 | 5 | 1000 | f3 |
| 6 | 6 | 750 | f6 | 54 | 6 | 500 | f4 |
| 7 | 7 | 500 | f7 | 55 | 7 | 750 | f5 |
| 8 | 8 | 1000 | f8 | 56 | 8 | 500 | f6 |
| 9 | 9 | 750 | f9 | 57 | 9 | 1000 | f7 |
| 10 | 10 | 500 | f10 | 58 | 10 | 750 | f8 |
| 11 | 11 | 1000 | f11 | 59 | 11 | 500 | f9 |
| 12 | 12 | 500 | f12 | 60 | 12 | 1000 | f10 |
| 13 | 2 | 750 | f13 | 61 | 2 | 500 | f11 |
| 14 | 3 | 500 | f14 | 62 | 3 | 750 | f12 |
| 15 | 4 | 1000 | f15 | 63 | 4 | 500 | f13 |
| 16 | 5 | 750 | f16 | ⋮ | ⋮ | ⋮ | ⋮ |
| 17 | 6 | 500 | f17 | 4197 | 10 | 1000 | f47 |
| 18 | 7 | 1000 | f18 | 4198 | 11 | 500 | f48 |
| 19 | 8 | 500 | f19 | 4199 | 12 | 750 | f49 |
| 20 | 9 | 750 | f20 | 4200 | 1 | 500 | f50 |
| 21 | 10 | 500 | f21 | 4201 | 1 | 1000 | f1 |
| 22 | 11 | 1000 | f22 | | | | |
| 23 | 12 | 750 | f23 | | | | |
| 24 | 1 | 500 | f24 | | | | |
| ⋮ | ⋮ | ⋮ | ⋮ | | | | |

*FIG. 7*

INCONTINENCE DETECTION SYSTEM

CROSS REFERENCE

This application is a Divisional of U.S. patent application Ser. No. 15/968,028 entitled "Incontinence Detection System" filed on. May 1, 2018, now U.S. patent Ser. No. 10/349,881, which claims priority to U.S. Provisional Applications 62/622,243 filed on Feb. 21, 2018 and 62/638,478 filed on Mar. 5, 2018, the contents of all of which are incorporated herein by reference.

TECHNICAL FIELD

The subject matter described herein relates to incontinence detection devices, in particular to a system which includes an incontinence detection pad having an RFID tag and an RFID reader which interrogates the tag with spatially and temporally varying power settings.

BACKGROUND

Incontinence detection devices are used in health care facilities to detect if an occupant of a bed, i.e. a patient, has suffered an incontinence event (accidental discharge of urine and/or liquid fecal matter). Detection of incontinence is important for at least the following reasons. First, a caregiver who knows that a patient is subject to incontinence may be obligated to periodically wake the patient to determine if he has suffered an incontinence event. If an incontinence event has not occurred, the caregiver's intervention has needlessly interrupted the patient's sleep and occupied the caregiver's time. Second, the presence of fecal matter and urine on the bed is unsanitary and should be cleaned up as soon as possible. Third, prolonged exposure of the patient's skin to the moisture arising from the incontinence event increases the risk that the patient will develop a pressure ulcer. Early detection improves the likelihood that a caregiver will take corrective action (drying the patient and replacing soiled sheets and blankets) before the presence of the moisture can compromise the integrity of the patient's skin. Conversely, a detection system that issues numerous false alarms can discourage caregivers from responding as quickly as is desirable, and may even discourage caregivers from using the pad.

One type of incontinence detection system includes a pad that a caregiver places on the mattress of the bed, underneath the patient. The pad has a Radio Frequency Identification (RFID) circuit comprised of a passive RFID tag connected to electrical conductors that branch out from the tag. The system also includes an RFID reader which interrogates the tag.

The tag responds to interrogations from the reader by generating a return signal whose information content includes a moisture status indicator. When the pad is dry the RFID circuit is open, and the moisture status indicator in the return signal indicates the dry status of the pad. When an incontinence event occurs, the liquid moisture closes the circuit so that the moisture status indicator indicates the wet status of the pad.

The reader is adapted to communicate with a destination other than the tag. Upon receiving the return signal, the reader can make a report to the destination of the wet/dry status of the pad. In one example the destination is a light switch and the report is a signal that operates the switch so that the light indicates the status of the pad. In another example the destination is a nurse call system and the report is a message displayed at a nurse station.

One difficulty with such a system is that patient movement can shift the position of the pad on the bed, and/or the patient may move relative to the pad and the reader. Consequently the spatial relationship among the patient, the reader, and the tag may change, or the patient's position may interfere with clear communication between the reader and the tag. This can result in the interrogation signal from the reader being too weak to be useful when it arrives at the tag or the return signal from the tag being too weak to be useable by the reader.

In principle, difficulties arising from weak signals can be addressed by generating a more powerful signal at the reader and producing a correspondingly more powerful return signal from the tag. However in practice, the use of a more powerful signal can cause the RFID circuit to indicate a false wet condition. Moreover, a more powerful signal may expose the patient to more radio frequency (RF) energy than is prudent or more than is permitted by safety regulations.

Therefore, it is desirable to provide an incontinence detection device that reliably detects actual incontinence events, is not likely to produce false alarms (erroneous indications that the pad is wet) and that operates at modest levels of RF energy.

SUMMARY

A system for detecting an incontinence event includes a pad which is deployable on a mattress and which, as deployed, has a first conductor and a second conductor which are not in electrical communication with each other. The system also incudes an RFID reader subsystem having a processor and an array of two or more spatially distributed antennas. The system is adapted to A) command transmission of energy from the antenna array at a variety of powers and at various frequencies, B) monitor the antenna array for a return signal resulting from the spatially and temporally varying transmission, and C) communicate a WET or DRY status to a destination. The WET or DRY status depends on a moisture status indicator of the return signal.

The present invention may comprise one or more of the features recited in the appended claims and/or one or more of the features described in this specification or combinations thereof.

BRIEF DESCRIPTION OF THE DRAWINGS

The foregoing and other features of the various embodiments of the incontinence detection system described herein will become more apparent from the following detailed description and the accompanying drawings in which:

FIG. 7 shows an example of the actions of the processor of FIG. 1 in tabular form.

DETAILED DESCRIPTION

Figure 1:
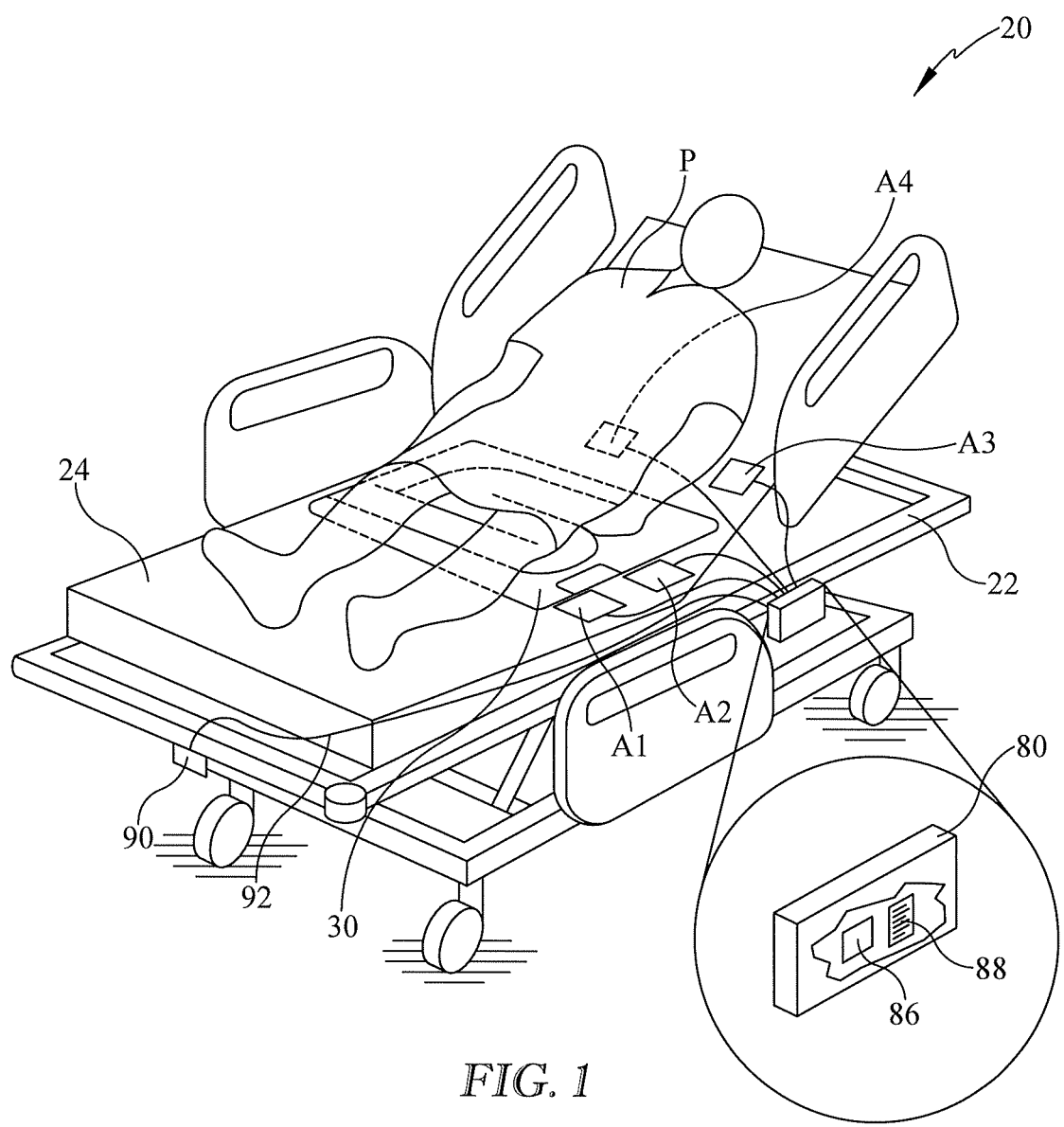
FIG. 1 is a view showing a hospital bed, a patient lying on the bed and an incontinence detection system comprised of a pad, and an RFID reader subsystem which includes a processor that responds to machine readable instructions.

In this specification, features similar to or the same as features already described may be identified by reference characters or numerals which are the same as or similar to those previously used.

Figure 3:
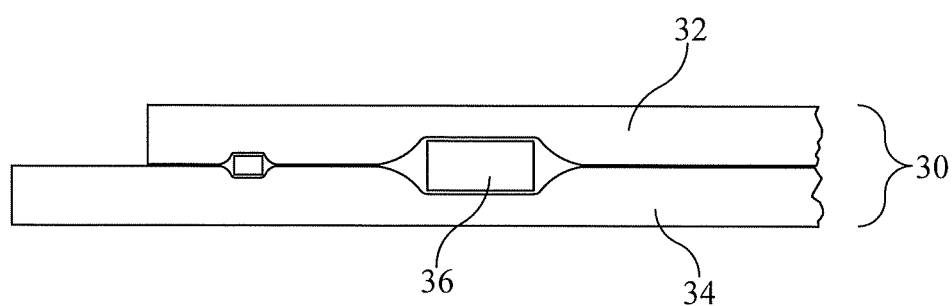
FIG. 3 is schematic cross sectional view taken along 3-3 of FIG. 2 showing upper and lower layers of the pad, an RFID tag, and a conductor.
Figure 2:
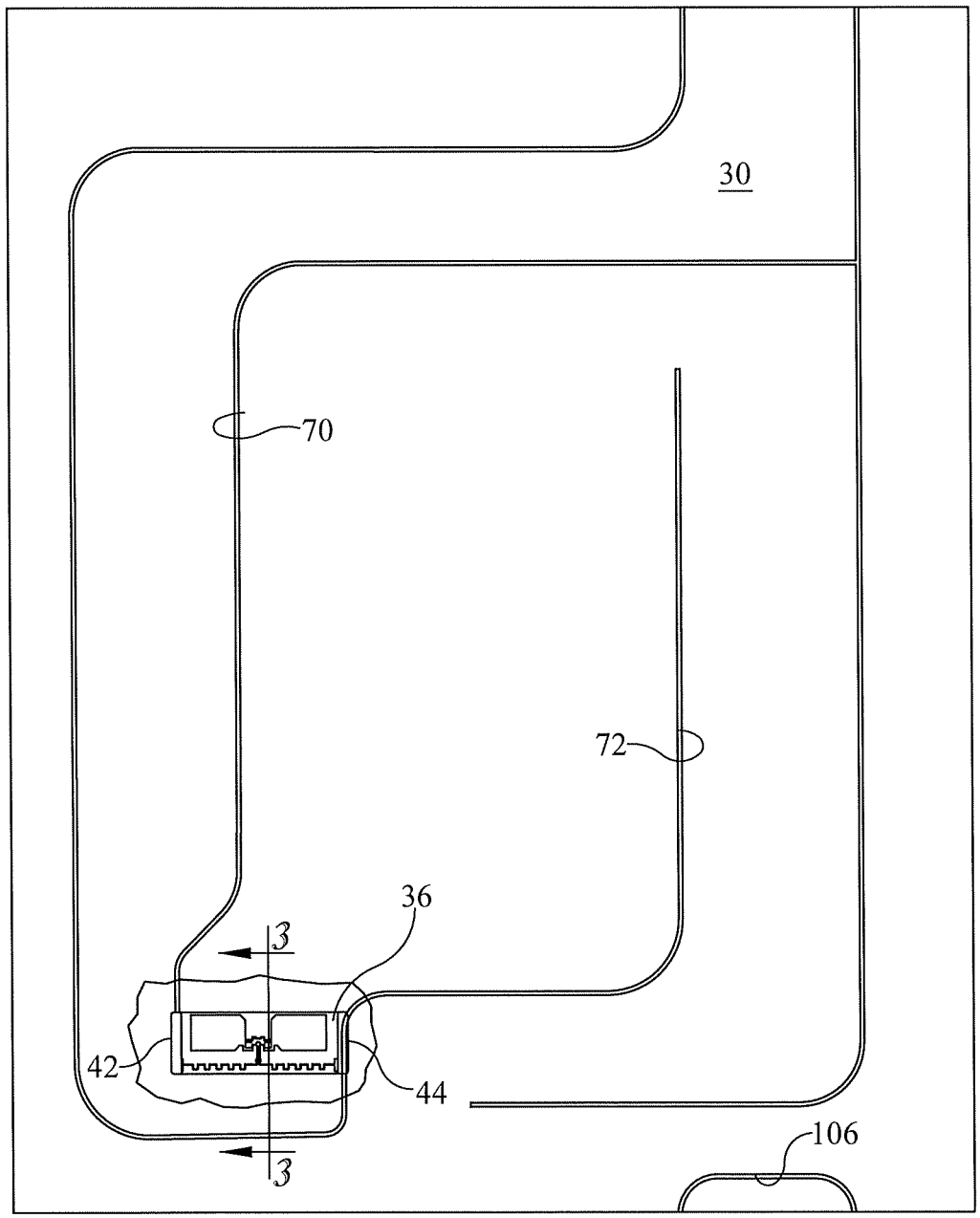
FIG. 2 is plan view of the pad of FIG. 1 as seen from above showing an open circuit comprised of first and second conductors and also showing an RFID tag, also referred to as an RFID inlay.

Referring to FIGS. 1-3 a hospital bed 20 includes a bed frame 22 and a mattress 24. An incontinence detection system comprises a pad 30 which includes an upper, moisture permeable layer 32, a lower, moisture absorbant layer 34, and an RFID tag or inlay 36 between the layers. FIG. 1 shows a single pad 30, however multiple pads distributed on the mattress may be used. This specification describes a system in which the RFID tag is passive, i.e. it does not have its own power supply but instead harvests power from an interrogation signal produced by an RFID reader (described below). However a powered tag is also suitable.

Figure 4:
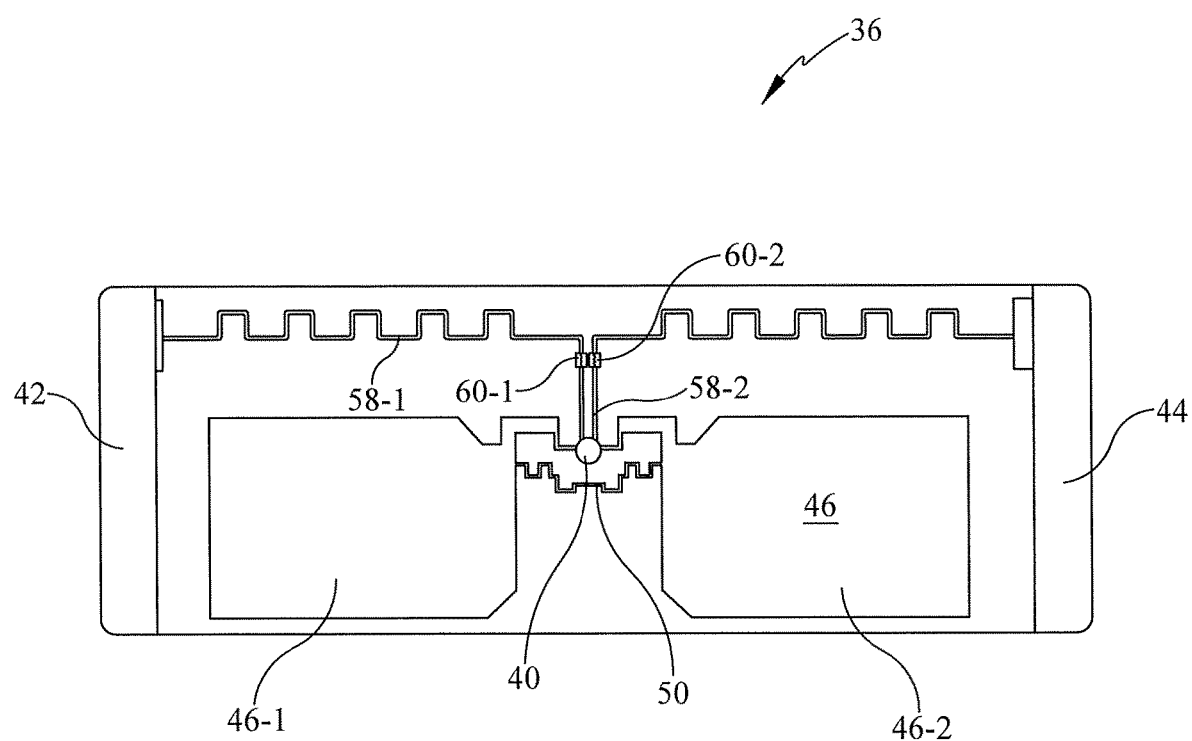
FIG. 4 is a magnified view of the RFID inlay of FIG. 2.
Figure 5:
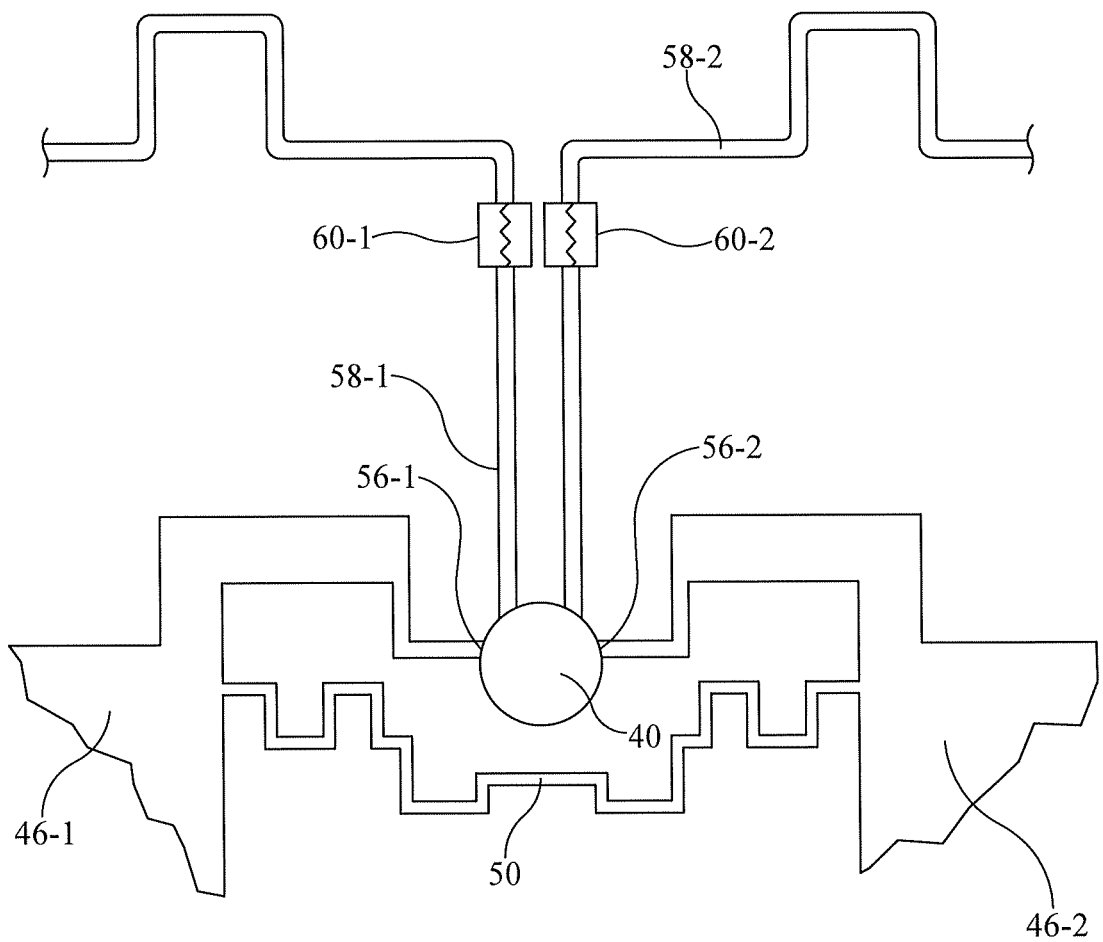
FIG. 5 is a more magnified view of a portion of the inlay of FIG. 4.

Referring principally to FIGS. 3-5, the RFID inlay includes an inlay processor 40, a first terminal 42, a second terminal 44, an inlay antenna 46 having first and second ears 46-1, 46-2, and a bridge 50 extending between the ears. Processor 40 is referred to as an inlay processor to distinguish it from an RFID reader processor 86 described below. Antenna 46 is referred to as an inlay antenna to distinguish it from an RFID reader antenna 82 described below.

Each antenna ear 46-1, 46-2, is individually connected to processor 40 at connections 56-1, 56-2. First and second terminals 42, 44 are connected to inlay processor 40 by first and second electrical paths 58-1, 58-2 respectively. One or both of electrical paths 58-1, 58-2 is configured to guard against RF energy that impinges on one or both pad conductors (described below) from coupling to the inlay antenna. In the illustrated tag, anti-coupling is provided by resistors 60-1, 60-2 in electrical paths 58-1, 58-2 and a nonlinear path geometry such as the illustrated square wave path geometry. It may be sufficient to use either a resistor or a nonlinear geometry rather than both.

The pad, as deployed on a mattress and in a state of being ready for use, includes an open circuit comprised of a first conductor 70 extending from first terminal 42 of the inlay, and a second conductor 72 extending from second terminal 44 of the inlay. The phrase "open circuit" is used in its conventional sense, recognizing its status as a misnomer due to the absence of a complete circuit through which electrical current can flow.

The system also includes an RFID reader subsystem comprised of an RFID reader or interrogator 80 and two or more antennas A1, A2, A3, A4. The reader and antennas are removably affixed to bed frame 22. Each antenna is adapted to radiate and receive electromagnetic energy, specifically radio frequency (RF) energy. The example RFID reader subsystem of the illustration includes four antennas spatially distributed on the bed frame, three along the left side of the bed frame and one about midway between the left and right edges of the frame. ("Left" and "right" are taken from the perspective of a supine patient such as patient P of FIG. 1.)

The RFID reader subsystem also includes a processor 86 (FIG. 1, inset) which executes machine readable instructions 88 in order to reliably detect incontinence without producing an unsatisfactory number of false alarms and without exposing the patient to excessive amounts of RF energy. In particular the processor selects an antenna pair from an ordered list antenna pairs in which one member of the pair is a send antenna and the other member is a receive antenna. The processor also selects a transmit power setting from an ordered list of transmit powers and selects a transmit frequency from an ordered list of frequencies. The processor commands transmission of energy from the send antenna of the selected antenna pair at the selected frequency and power setting.

The system monitors the selected receive antenna for a return signal from the inlay. The information content of the return signal includes at least a moisture status indicator, and may include other information such as received signal strength indicator (RSSI) and tag identifier. One example of a moisture status indicator is an information bit which takes on one value (e.g. 0) if the pad is dry and the opposite value (1) if the pad is wet. The moisture status indicator distinguishes between perceived presence and perceived absence of moisture at the pad. The system issues a report to a destination. The report includes a WET or DRY indication based on the status indicator of a sample of one or more return signals.

The incontinence detection system also includes a light 90 attached to bed frame 22 and connected to reader 80 by wire 92.

Table 1, below is an example of an ordered list of candidate send/receive antenna pairs for the four antenna system of FIG. 1, and an index i for each pair. The list of antenna pairs contains $N_{AP}$ members where $N_{AP}=24$. In general the ordered list of antenna pairs includes at least one occurrence of every possible send/receive pairing. The example ordered list of Table 1 includes two occurrences of every possible send/receive pairing.

TABLE 1

| index (i) | Send Antenna | Receive Antenna |
| --- | --- | --- |
| 1 | A1 | A2 |
| 2 | A1 | A3 |
| 3 | A1 | A4 |
| 4 | A2 | A1 |
| 5 | A2 | A3 |
| 6 | A2 | A4 |
| 7 | A3 | A1 |
| 8 | A3 | A2 |
| 9 | A3 | A4 |
| 10 | A4 | A1 |
| 11 | A4 | A2 |
| 12 | A4 | A3 |
| 13 | A1 | A3 |
| 14 | A1 | A4 |

TABLE 1-continued

| index (i) | Send Antenna | Receive Antenna |
|---|---|---|
| 15 | A2 | A1 |
| 16 | A2 | A3 |
| 17 | A2 | A4 |
| 18 | A3 | A1 |
| 19 | A3 | A2 |
| 20 | A3 | A4 |
| 21 | A4 | A1 |
| 22 | A4 | A2 |
| 23 | A4 | A3 |
| 24 | A1 | A2 |

Entries 1-12 of Table 1 are a first ordered sublist of antenna pairings which includes every possible pairing of a single send antenna and a single receive antenna for the four antenna arrangement of FIG. 1 with the condition that an antenna selected as the send antenna is not selected as the receive antenna and vice versa. Entries 1-12 are ordered so that as one advances down the list the same send antenna is repeated until it has been paired with all three of the other antennas (ordered by increasing value of the numerical suffix following the letter "A"), each serving as a receive antenna. Then another antenna is selected as the send antenna and repeated until it has been paired with all three of the other antennas, each serving as a receive antenna. The antenna assignments are arbitrary, i.e. any one of the antennas seen in FIG. 1 can be A1, any one can be A2, any one can be A3, and any one can be A4.

Entries 13-24 of Table 1 are a second ordered sublist of antenna pairings which includes every possible pairing of a single send antenna and a single receive antenna for the four antenna arrangement of FIG. 1 with the condition that an antenna selected as the send antenna is not selected as the receive antenna and vice versa). The antenna pairs of entries 13-23 of Table 1 are the same as the antenna pairs of entries 2-12 respectively; the antenna pair of entry 24 is the same as the antenna pair of entry 1. In other words, antenna pairs 13-24 are antenna pairs 1-12 repeated in the same order except that antenna pair A1/A2 appears at the end of the sequence instead of at the beginning. The second sublist may be referred to as an offset ordering of the first sublist. The offset ordering of the second sublist of Table 1 is a "one-offset" ordering because only one antenna pairing of the first sublist is moved to the end of the sublist. Offset orderings other than one-offset can also be used (two-offset, three-offset, etc.) with the understanding that even numbered offsets may cause specific antenna pairs to be combined with the same even frequency (f2, f4, f6, . . . ) or the same odd frequency (f1, f3, f5, . . . ) more frequently than is desired.

More formally, the list of antenna pairs is made up of two sublists each having m members (a first sublist (antenna pairs 1-12) and a second sublist (antenna pairs 13-24)). Antenna pair q of the first sublist and antenna pair q−1 of the second sublist are the same antenna pair, with the exception that antenna pair m of the second sublist and antenna pair 1 of the first sublist are the same antenna pair. In Table 1, m=12. By way of example the seventh member (q=7) of the first sublist (send/receive antennas A3/A1 at i=7) and the sixth member (q−1=6) of the second sublist (send/receive antennas A3/A1 at i=18) are the same as each other except that the twelfth member of the second sublist (send/receive antennas A1/A2 at i=24) and the first member of the first sublist (send/receive antennas A1/A2 at i=1) are the same as each other.

Although each antenna pair appears twice in the antenna pair listing of Table 2, the two appearances of any given send/receive pair are considered to be separate selections. For example antenna pair A2/A4 at i=6 and antenna pair A2/A4 at i=17 are different selections, not the same selection.

Table 2, below, is an example of an ordered list of predefined transmit power settings expressed in milliwatts (mW), and an index j for each power setting. The list of power settings has $N_P$ members representing $N_{UP}$ unique power settings. $N_{UP}$ is less than $N_P$. As a result the ordered list of transmit power settings includes at least one transmit power repetition. $N_{UP}$ is greater than or equal to two. In the example $N_{UP}=3$ and $N_P=7$. The 1000 mW power is repeated once for a total of two occurrences; the 750 mW power setting is repeated once for a total of two occurrences; the 500 mW power setting is repeated twice for a total of three occurrences.

TABLE 2

| index (j) | Power (mW) |
|---|---|
| 1 | 1000 |
| 2 | 750 |
| 3 | 500 |
| 4 | 1000 |
| 5 | 500 |
| 6 | 750 |
| 7 | 500 |

Although each power setting in the listing of Table 2, appears at least twice, repeat appearances of any given power setting are considered to be separate selections. For example the 500 mW power setting at j=3, the 500 mW power setting at j=5, and the 500 mW power setting at j=7 are different selections, not the same selection.

Table 3, below, is an example of an ordered list of predefined candidate transmit frequencies settings expressed in megahertz (MHz), and an index k for each frequency. The list of candidate frequencies contains $N_F$ members representing $N_{UF}$ different frequencies where $N_F \geq 2$. In the example $N_F=N_{UF}=50$, i.e. each frequency in the list of frequencies differs from all the other frequencies in the list of frequencies. The example frequencies are taken from the 902-928 MHz frequency band of the electromagnetic spectrum. A smaller band, for example 902-915 or 915-928 MHz, may also be suitable provided that for a product for use in the United States at the present time, the list of candidate frequencies contains $N_F$ members representing $N_{UF}$ different frequencies, such that $N_F=N_{UF}=50$, in order to ensure compliance with existing regulations of the Federal Communications Commission (FCC). The order of the frequencies as one advances from k=1 to k=50 is determined randomly or pseudorandomly. However once determined, that order remains fixed. As a result, and as seen by the example numerical values, the randomly or pseudorandomly determined frequencies are highly likely to be nonmonotonic with respect to k. Indeed, a monotonic sequence would be unsatisfactory at least because it would be noncompliant with current regulations of the United States FCC. Therefore, existing regulations compel the use of a nonmonotonic sequence.

TABLE 3

| index (k) | Example Frequency (MHz) |
|---|---|
| 1 | f1 = 917.4 |
| 2 | f2 = 914.5 |
| 3 | f3 = 922.0 |
| 4 | f4 = 923.7 |
| . | |
| . | |
| . | |
| 50 | f50 = 907.6 |

Figure 6:
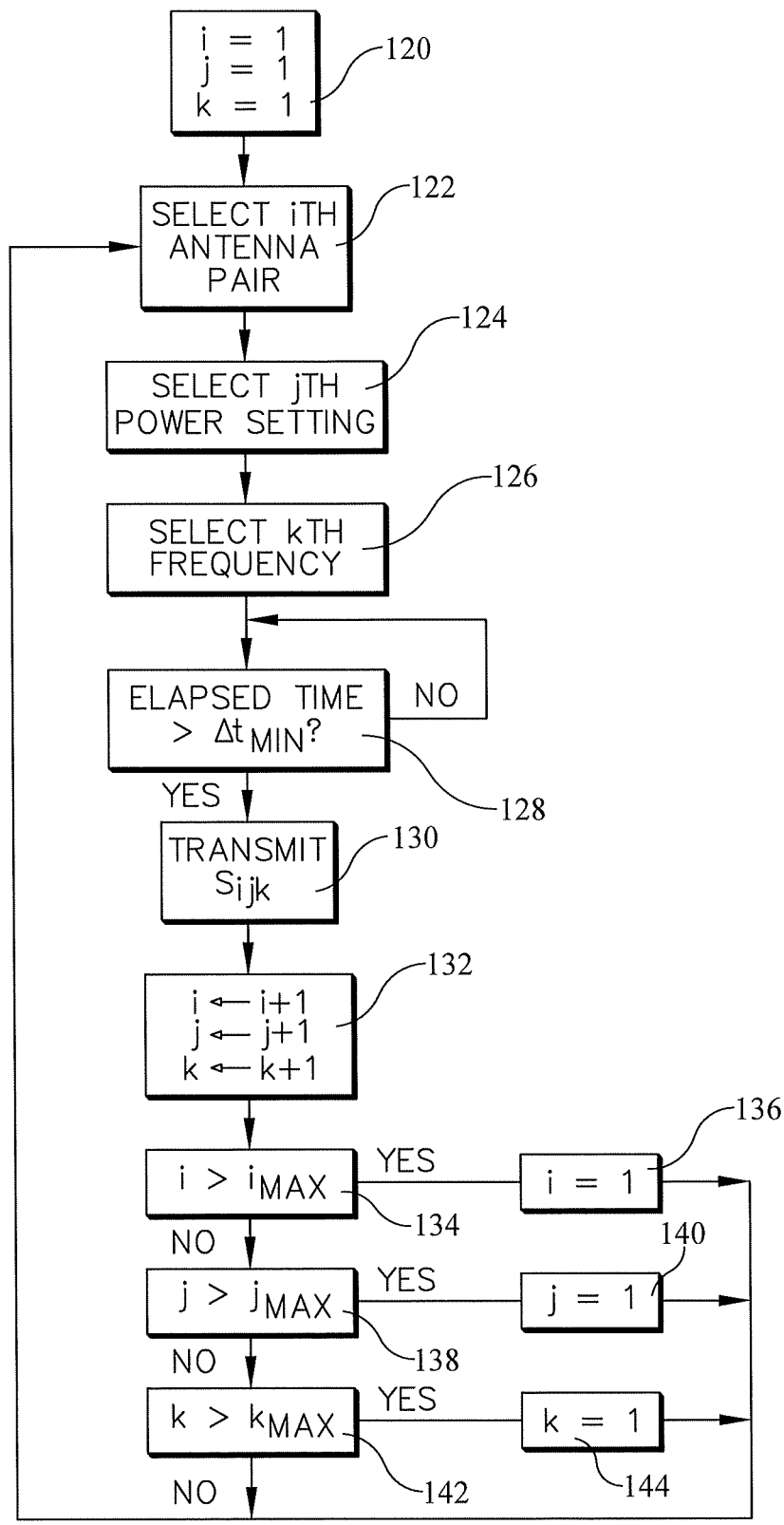
FIG. 6 is a block diagram showing an embodiment of a method carried out by the processor of FIG. 1 in response to the machine readable instructions of FIG. 1.

FIG. 6 is a block diagram showing an embodiment of the method carried out by processor 86 in response to machine readable instructions 88. At block 120 indices i, j, k are each set to 1. At block 122 the method selects the $i_{th}$ antenna pair. At block 124 the method selects the $j_{th}$ power setting. At block 126 the method selects the $k_{th}$ frequency.

Disregarding block 128 for the moment, at block 130 the method transmits a signal $Si_{ijk}$. Signal $S_{ijk}$ is a signal transmitted from the send antenna of antenna pair i at power setting j and frequency k. With index values i, j, k equal to 1, 1, 1, the system commands transmission of a signal from antenna A1 of pair A1/A2 at f1 (e.g. 917.4 Mhz) at 1000 mW.

The method then advances to block 132 where it increments each current value of i, j, and k by one.

The method then advances to block 134 where it tests if index i, as incremented at block 132, exceeds a value $i_{max}$. If so, all the antenna pairings of Table 1 have been used once, and in the order shown. Therefore the method advances to block 136 where it resets i to one and advances out of block 136. If not, the method retains the incremented value of i from block 132 and branches to block 138.

At block 138 the method tests if index j, as incremented at block 132, exceeds a value $j_{max}$. If so, all the power settings of Table 2 have been used once, and in the order shown. Therefore the method advances to block 140 where it resets j to one and advances out of block 140. If not, the method retains the incremented value of j from block 132 and branches to block 142.

At block 142 the method tests if index k, as incremented at block 132, exceeds a value $k_{max}$. If so, all the frequencies of Table 3 have been used once, and in the order shown. Therefore the method advances to block 144 where it resets k to one and advances out of block 144. If not, the method advances out of block 142.

After carrying out the appropriate actions at blocks 132, 134, 136, 138, 140, 142, and 144, the method returns to block 122 with an updated set of i, j, k values and repeats the above described steps. Specifically, the method repeats the select and transmit steps at blocks 122, 124, 126, and 130 with i replaced by an incremented value of i, j replaced by an incremented value of j, and k replaced by an incremented value of k provided that if any of the values of i, j, or k, as incremented at block 132, exceeds $i_{max}$, $j_{max}$, $k_{max}$ respectively (as tested at blocks 134, 138, 142), the excessive value is replaced by one (blocks 136, 140, 144).

Each arrival at block 136 marks the conclusion of one antenna pair cycle. Each arrival at block 140 marks the conclusion of one power setting cycle. Each arrival at block 144 marks the conclusion of one frequency cycle.

The sequence of actions of FIG. 6 results in transmission, at block 130, of a signal from the first send antenna of Table 1 at the first power setting of Table 2 at the first frequency of Table 3. This is followed by transmission of a signal from the second send antenna of Table 1 at the second power setting of Table 2 at the second frequency of Table 3, and so forth. Each time the system reaches the end of a list it returns to the beginning of that list while continuing to step through the entries of the other lists.

FIG. 7 illustrates the above described actions of processor 86 in tabular form for the case of $i_{max}$=24, $j_{max}$=7 and $k_{max}$=50 (or equivalently, $N_{AP}$=24, $N_P$=7 and $N_F$=50). The illustration shows 4201 passes through the block diagram of FIG. 6. Each heavy horizontal line spanning across an antenna pair, power setting or frequency column represents an antenna pair cycle (arrival at block diagram block 136) a power setting cycle (arrival at block diagram block 140) or frequency cycle (arrival at block diagram block 144). The dashed lines spanning across the antenna pair column represents the boundary between two antenna pair sublists.

In the above example Tables 1-3 include twelve possible send/receive antenna pairings, fifty different frequencies, and three different power settings. Therefore there are 1800 unique groupings of antenna pair, frequency, and power setting. In the first 4200 passes through the block diagram of FIG. 6, the sequence in which the groupings appear does not exhibit any periodicity. After 4200 passes the groupings are repeated, i.e. 4200 passes is a complete cycle. No quotient of any two of $N_{AP}$, $N_P$, and $N_F$ is an integer. Equivalently, no quotient of any two of $i_{max}$, $j_{max}$, $k_{max}$ is an integer. As a result, during any complete cycle no grouping of a given antenna pair, a given power, and a given frequency is used so frequently that its use dominates the use of any other grouping of a given antenna pair, a given power, and a given frequency. Stated differently, during any complete cycle each grouping of a given antenna pair, a given power, and a given frequency is used about the same number of times. For example the grouping of send/receive antenna pair A4/A2, frequency f32, and transmission power 750 mW is used only twice in 4200 passes and the grouping of send/receive antenna pair A1/A2, frequency f41, and transmission power 1000 mW is used only three times in the 4200 passes. In any set of 4200 transmissions, each grouping is used at least once. No grouping is used more than three times. Six hundred of the possible groupings are used only three times, and 1200 of the groupings are used only two times. In principle the antenna pairs could be ordered the same way in both subsets however this would result in a greater number of repetitions of identical groupings of send/receive antenna, frequency and power setting.

Returning now to FIG. 6, block 128 may selectively delay the execution of the signal transmission at block 130 relative to the immediately preceeding signal transmission at block 130. In the illustrated embodiment the processor inquires, at block 128, whether a predesignated interval of time has elapsed since the immediately preceeding execution of block 130. If so the processor immediately advances to block 130. If not, the processor waits until the predesignated interval of time has elapsed before advancing to block 130. The delay enforces an upper limit on the temporal concentration of the RF energy to which the patient is exposed. In other words the delay ensures that the patient's exposure to RF is spread out in time. Block 128 may be omitted if it is unnecessary to enforce a limit on RF exposure.

Figure 8:
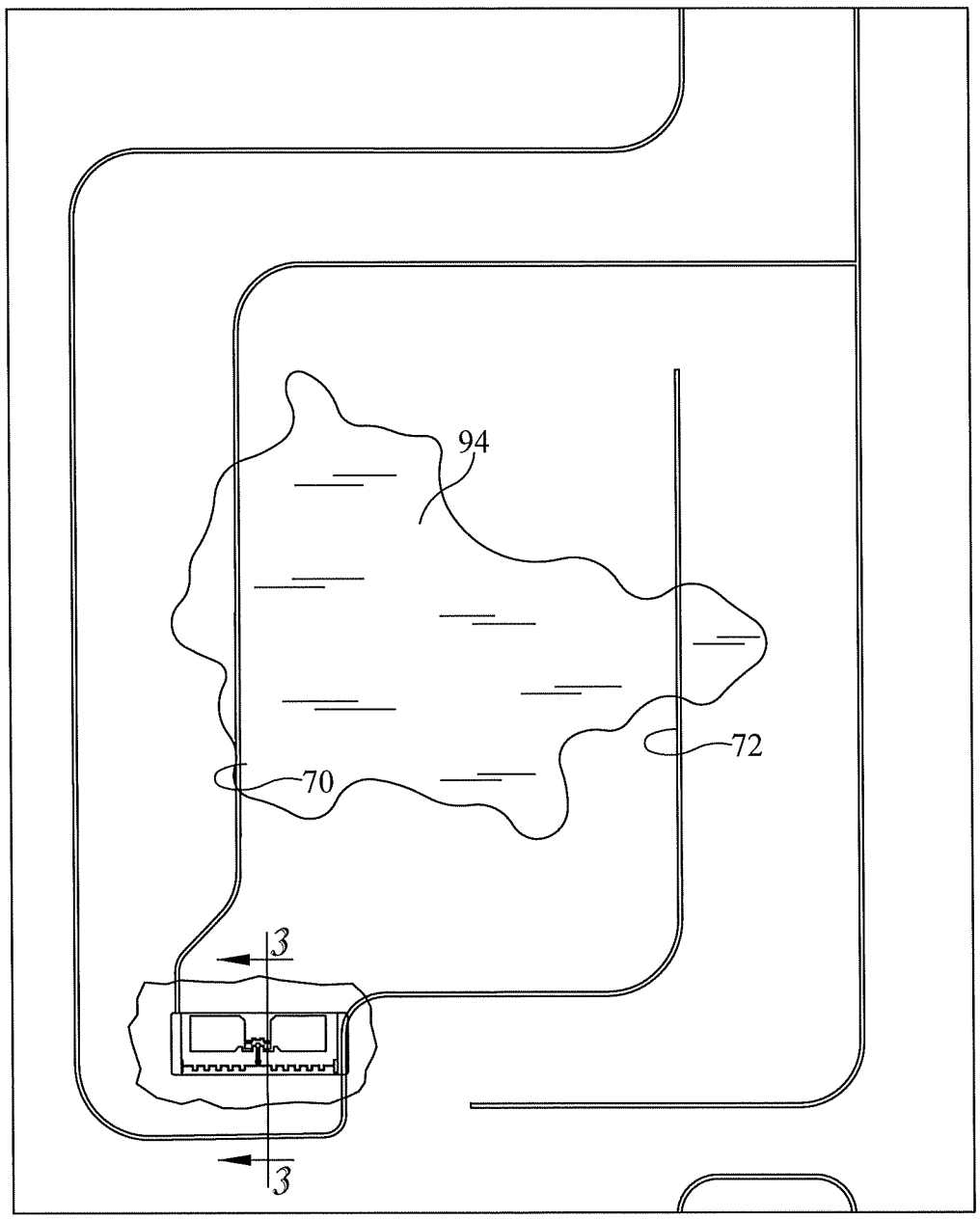
FIG. 8 shows the pad of FIG. 2 with a puddle of liquid whose presence may be the result of an incontinence event and which closes the circuit.
Figure 9:
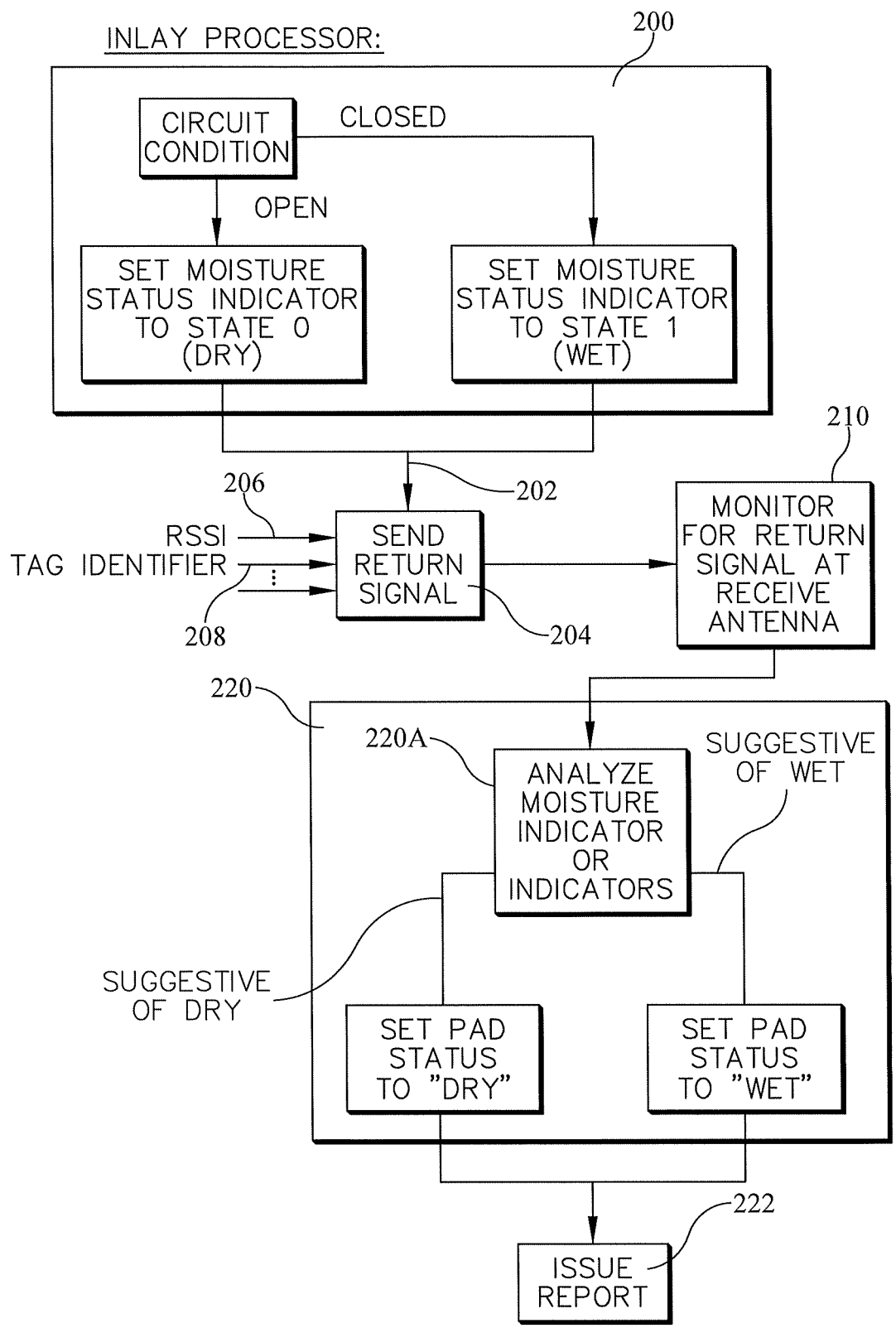
FIG. 9 is a flow diagram showing a moisture status indicator being set by the inlay of FIG. 1 and also showing a pad status indicator being set by the processor of FIG. 1.

FIG. 2 shows pad 30 with no liquid present at the pad. The circuit is open. FIG. 8 shows the pad with a puddle 94 of liquid whose presence may be the result of an incontinence event. The puddle bridges between conductors 70 and 72 thereby closing the circuit. Referring additionally to FIG. 9, the inlay processor 40 responds to the condition of the circuit (open or closed) at block 200 by setting a moisture status indicator 202 to a wet state (illustrated as "state 1") corresponding to the perceived presence of moisture at the pad due to a closed circuit or by setting the indicator to a dry state (illustrated as "state 0") corresponding to the perceived absence of moisture at the pad due to an open. The parameters of the detection system are selected so that closure of the circuit occurs only in the presence of a meaningful amount of liquid. By way of example, a designer may decide that the amount of liquid associated with an incontinence event is meaningful, but a few drops of a beverage spilled on the pad is not. Parameters of the system include spacing of the first and second conductors and how readily the pad promotes spatial distribution of liquid. For example a given quantity of liquid will be more likely to close the circuit of a mat with smaller spacing between the conductors and less likely to close the circuit of a mat with larger spacing between the conductors. That quantity of liquid is meaningful for the mat with the smaller conductor spacing.

Upon successfully receiving an interrogation signal from one of the reader antennas (A1, A2, A3, or A4 depending on which antenna is operating as the send antenna) the inlay responds at block 204 with a return signal which has an information content. The information content includes at least the moisture status indicator 202, and may include other information such as received signal strength indicator (RSSI) 206 and a tag identifier 208 which is unique to the tag, and therefore to the pad. Knowledge of the tag identifier may be useful when multiple pads are placed on the mattress instead of only a single pad.

During the above described interrogations of the tag by reader 80, the system monitors for the arrival of a return signal at the designated receive antenna (FIG. 9, block 210). Provided the return signal successfully arrives at the receive antenna (block 210; antenna A1, A2, A3, or A4 depending on which antenna is operating as the receive antenna) processor 86 inquires whether the moisture status indicator is consistent with a dry state of the pad or a wet state of the pad (block 220). At block 222 the processor issues a report to a destination. The report includes a WET indication or a DRY indication depending on the state of the moisture status indicator of the return signal. In one embodiment the indication of WET or DRY is based on a sample of multiple return signals rather than on a sample of one signal, hence the use of "indicator or indicators" at block 220A. In such an embodiment some of the moisture status indicators may be consistent with the presence of moisture while others are consistent with the absence of moisture. Indicators of mixed polarity may arise because of, for example, perspiration on the pad or transient noise in the system. A statistical analysis is used to reach a conclusion of whether the report issued at block 222 should report an indication of WET or DRY.

The report issued at block 222 may take different forms depending on the destination. One suitable destination for the report is a nurse call system where the report may take the form of a message appearing on a monitor display at a nurses' station.

Another suitable destination is an indicator light such as light 90 of FIG. 1, or more specifically a switch that operates the light. In one embodiment color and intermittancy are used as set forth below:
1) solid green light: a pad is present and is being monitored, but no moisture is detected,
2) flashing amber light: the pad is wet (the flashing amber light may be projected onto the floor,
3) solid white light: the system is operating but no pad is detected,
4) alternating white and green light: the system cannot operate effectively because more than a maximum number of pads is detected.

Figure 10:
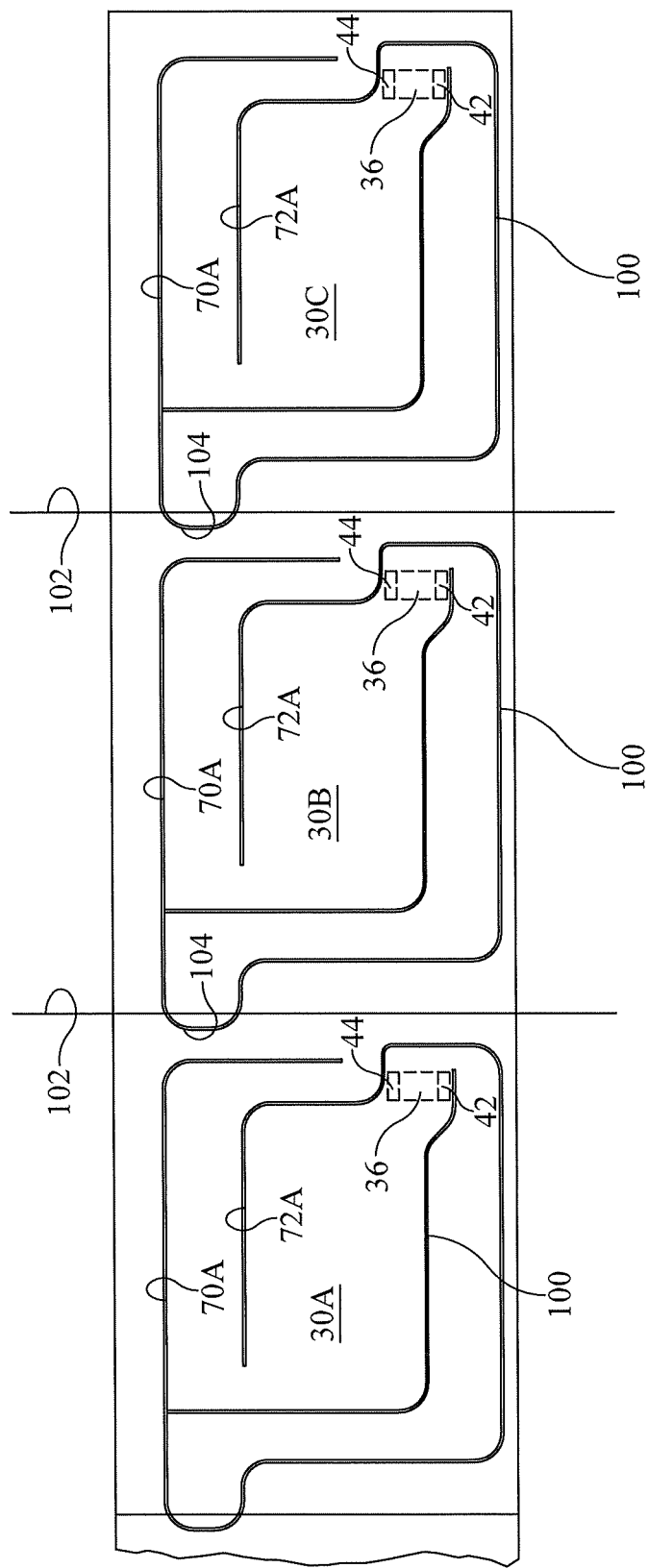
FIG. 10 is a plan view of a continuous sheet from which multiple pads can be cut.

FIG. 10 is a plan view showing one aspect of the manufacture of the pad. During manufacture multiple conductive paths 100 are printed on a continuous sheet. Cut lines 102 define notional edges of individual pad precursors 30A, 30B, 30C. Each path is connected to a tag (inlay) terminal 42, 44.

As can be seen by comparing FIG. 10 to FIG. 2, each conductive path 100 includes a predecessor 70A of first conductor 70, a predecessor 72A of second conductor 72. An arch 104 connects the predecessors. The arch extends past one of the notional edges defined by a cut line 102 so that the conductive path resides on two adjacent pad precursors (e.g. 30A and 30B or 30B and 30C). In effect, the predecessors 70A, 72A of first and second conductors 70, 72 are shorted together by the arch. During manufacture a test is performed in which the processor detects the short and therefore assures that the manufacturing process is proceeding correctly. In particular the short indicates that tag 36 is positioned correctly and is attached to the conductor predecessors correctly. The sheet is then cut at each cut line which opens the circuit of the finished pad. Each arch 104 of the uncut sheet remains as a remnant 106 on each finished pad (FIG. 2).

Figure 11:
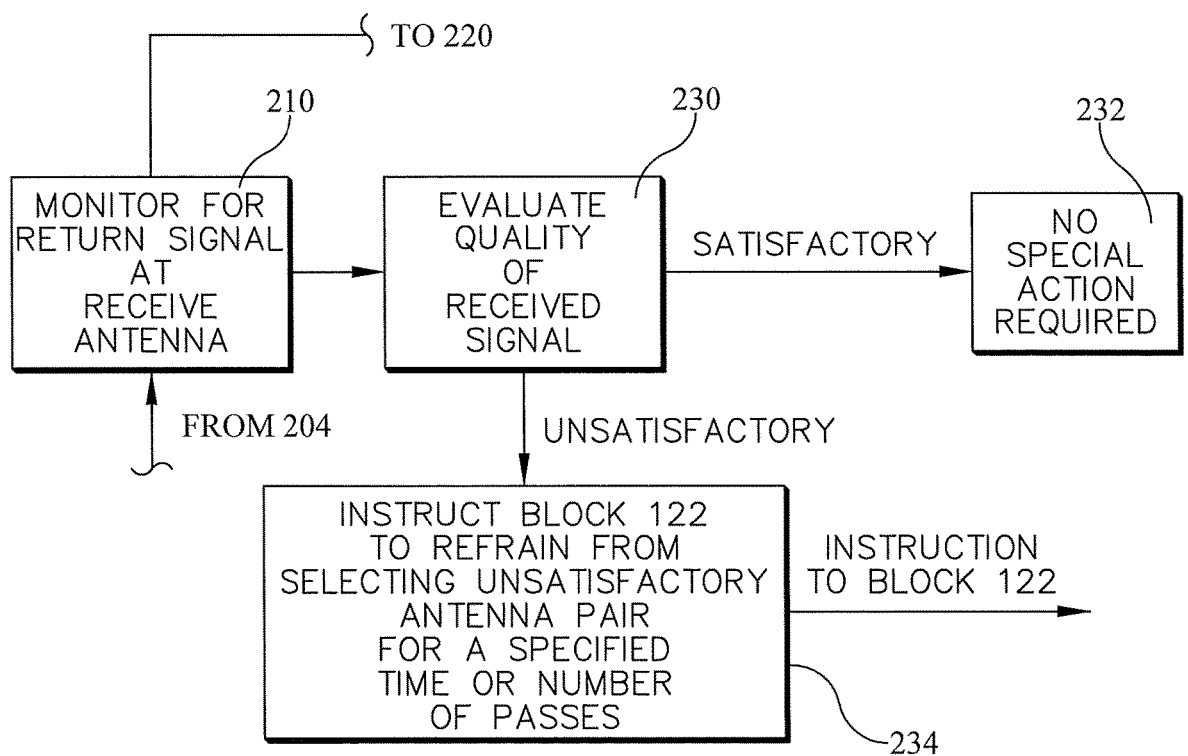
FIG. 11 is a block diagram showing a scheme for dynamic allocation of antenna pairs at block 122 of FIG. 6.

FIG. 11 illustrates a dynamic allocation scheme for selection of an antenna pair at block 122 of FIG. 6. The dynamic allocation scheme depends on the signal received at block 210 of FIG. 9. Block 210 of FIG. 9 is reproduced on FIG. 11.

At block 210 the branch to block 220 of FIG. 9 is augmented by a branch to block 230. At block 230 the system evaluates the quality of the received signal resulting from the use of the send/receive antenna pair selected at block 122. Signal quality may refer to signal strength and/or other signal properties such as noise content. The quality of the signal received as a result of using the selected antenna pair may be based on a single signal reception, or may be based on an analysis of multiple receptions.

If the signal is satisfactory the method branches to block 232 and takes no special action. If the signal is unsatisfactory the method branches to block 234. At block 234 the method instructs block 122 to refrain from future use of the unsatisfactory antenna pair for a specified period of time, or for a specified number of passes through the sequence of actions of FIG. 6. As a result, block 122 moves on to the next antenna pair not identified as having produced unsatisfactory results.

After the specified time has elapsed, or the specified number of passes has been executed, block 234 rescinds the prohibition on the use of the unsatisfactory antenna pair, allowing that pair (now considered to be not unsatisfactory) to be reincluded at block 122.

Figure 12:
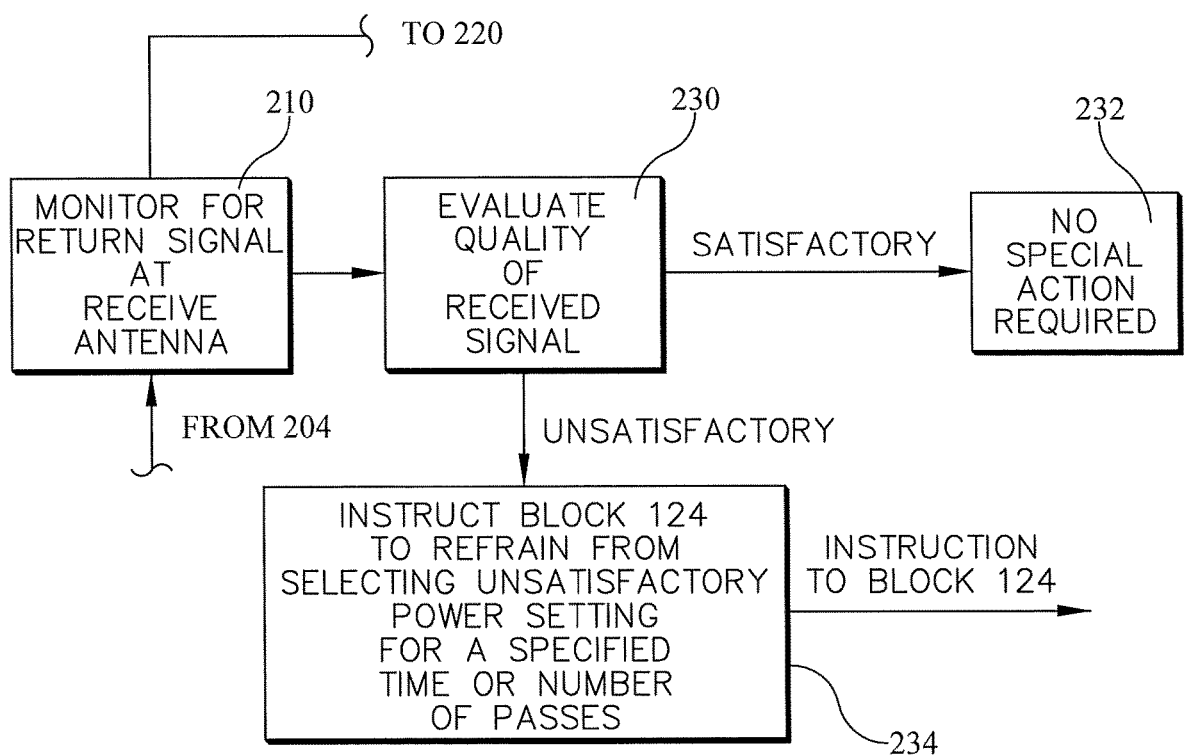
FIG. 12 is a block diagram showing a scheme for dynamic allocation of antenna pairs at block 124 of FIG. 6.

FIG. 12 illustrates a dynamic allocation scheme for selection of transmit power at block 124 of FIG. 6. The dynamic allocation scheme depends on the signal received at block 210 of FIG. 9. Block 210 of FIG. 9 is reproduced on FIG. 12. The method of FIG. 12 is analogous to that just described in connection with FIG. 11, but operates on transmit power selection rather than antenna pair selection.

Figure 13:
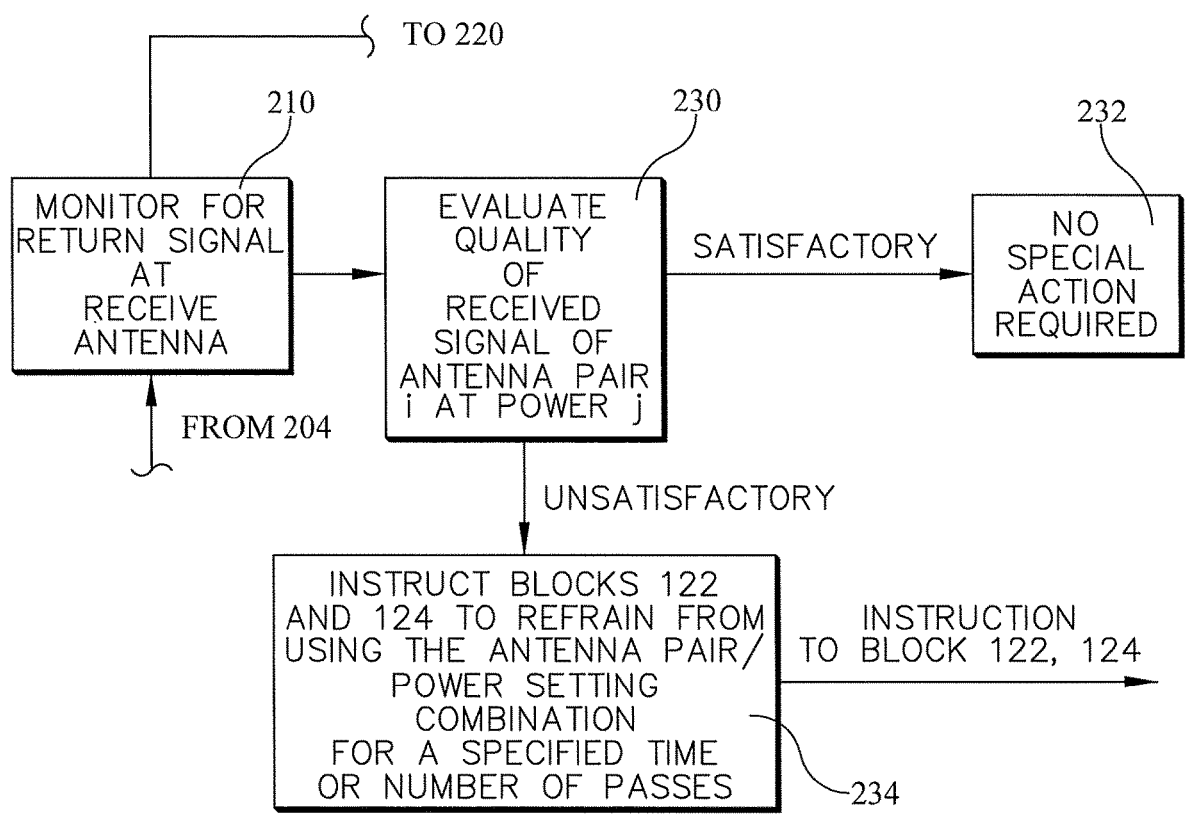
FIG. 13 is a block diagram showing a scheme for dynamic allocation of antenna pairs/power setting combinations at blocks 122 and 124 of FIG. 6.

FIG. 13 is another block diagram similar to that of FIG. 11. At block 230, the method of FIG. 13 evaluates the quality of the received signal resulting from the use of the send/receive antenna pair selected at block 122 at the power setting selected at block 124. Signal quality may refer to signal strength and or other signal properties such as noise content. The quality of the signal received as a result of using the selected antenna pair in combination with the selected power setting may be based on a single signal reception, or may be based on an analysis of multiple receptions.

If the signal is satisfactory the method branches to block 232 and takes no special action. If the signal is unsatisfactory the method branches to block 234. At block 234 the method instructs blocks 122, 124 to refrain from future use of the unsatisfactory antenna pair/power setting combination for a specified period of time, or for a specified number of passes through the sequence of actions of FIG. 6. As a result, blocks 122 and 124 move on to the the next antenna pair/power setting combination not identified as having produced unsatisfactory results.

After the specified time has elapsed, or the specified number of passes has been executed, block 234 rescinds the prohibition on the use of the unsatisfactory antenna pair/power setting combination, allowing that combination (now considered to be not unsatisfactory) to be reincluded by blocks 122 and 124.

Except as described above, the method of FIG. 6 is unaffected by the use of the dynamic allocation scheme of FIG. 11 or FIG. 12.

To the extent that doing so complies with government regulations, a method which evaluates the quality of the received signal resulting from the use of the send/receive antenna pair selected at block 122 at the frequency selected at block 126 may also be used.

In general terms, the system includes pad 30, an RFID reader subsystem as already described, and a processor adapted to command spatially and temporally varying transmission of energy from the antenna array at a variety of powers and at various frequencies. The system monitors the antenna array for a return signal resulting from the spatially and temporally varying transmission. The return signal has a moisture status indicator which indicates whether or not liquid is present on the pad. The system communicates a WET or DRY status to a destination. the reported WET or DRY status depends on the moisture status indicator.

In summary, the above described system employs spatially and temporally varying interrogation signals. The spatial variation increases the likelihood that a usable interrogation signal will arrive at the tag and that one of the antennas will receive a usable return signal even though the spatial relationship among the reader antennas, the patient, and the pad (tag) can change. The use of various power settings, in comparison to the exclusive use of the highest power, ensures that the patient is not always exposed to the maximum amount of RF energy and helps avoid the false wet indications associated with higher power while also using the high power setting often enough that the reader and tag can successfully communicate even in cases where the medium and lower power settings are inadequate.

Although this disclosure refers to specific embodiments, it will be understood by those skilled in the art that various changes in form and detail may be made without departing from the subject matter set forth in the accompanying claims. In addition, although this disclosure presents the incontinence detection system in the context of a health care setting and a patient, the system defined by the accompanying claims can be used in other settings and/or in connection with persons who might not qualify as patients.

We claim:

1. A system for detecting an incontinence event comprising:
   a pad which is deployable on a mattress and which, as deployed, has a first conductor and a second conductor and in which the first conductor and the second conductor are not in electrical communication with each other;
   an RFID reader subsystem having a processor and an array of two or more spatially distributed antennas, each member of the antenna array being adapted to radiate and receive electromagnetic energy, the system adapted to:
   A) command spatially and temporally varying transmission of energy from the antenna array at a variety of powers and at various frequencies, wherein the varying transmissions of energy include transmissions at a high power level, a low power level, and a medium power level that is an average of the high and low power levels, wherein the low power level is half of the high power level;
   B) monitor the antenna array for a return signal resulting from the spatially and temporally varying transmission, the return signal having an information content which includes a moisture status indicator which indicates whether or not liquid is present on the pad; and
   C) communicate a WET or DRY status to a destination, the WET or DRY status depending on the moisture status indicator.

2. The system of claim 1 wherein electrical communication is established between the first and second conductors if a meaningful quantity of liquid is present on the pad.

3. The system of claim 1 wherein the processor is adapted to carry out steps A, B, and C.

4. The system of claim 1 wherein:
   the processor selects a send/receive antenna pair of the antenna array from an ordered list of send/receive antenna pairs, the ordered list defining one member of the pair as a send antenna and the other member of the pair as a receive antenna;
   the transmission of step A is carried out with the send antenna;
   the monitoring of step B is carried out with the receive antenna; and
   the ordered list of antenna pairs includes at least one occurrence of every possible send/receive antenna pairing of the antennas of the antenna array.

5. The system of claim 4 wherein the ordered list of antenna pairs includes a first ordered sublist of antenna pairs and a second ordered sublist of antenna pairs, the ordering of the second sublist differing from the order of the first sublist.

6. The system of claim 5 wherein the ordering of the second sublist is an offset ordering.

7. The system of claim 1 wherein:
   the processor selects the transmit power to be used at step A from an ordered list of transmit powers, the list including at least one transmit power repetition.

8. The system of claim 1 wherein execution of step A is selectively delayed relative to the immediately preceding execution of step A.

9. The system of claim 1 wherein the indication of WET or DRY is based on a sample of more than one return signal and does not require the state of the moisture status indicator to be the same in all of the return signals of the sample.

10. The detection system of claim 1 wherein the destination comprises one or more of an indicator light and a nurse call system.

11. The detection system of claim 1 comprising multiple pads each having an identity, and wherein the information content of the return signal from each pad includes a pad identifier and the report includes a WET or DRY indication accompanied by the pad identifier.

12. The system of claim 1 wherein the moisture indicator indicates the presence of moisture at the pad if electrical communication is established between the first conductor and the second conductor.

13. The system of claim 12 wherein the moisture indicator indicates absence of moisture at the pad if electrical communication is not established between the first conductor and the second conductor.

14. The system of claim 1 wherein the high, medium, and low power levels are each 1000 milliWatts (mW) or less.

15. A system for detecting an incontinence event comprising:
   a pad which is deployable on a mattress and which, as deployed, has an open circuit comprised of a first conductor extending from a first terminal of an RFID inlay, and a second conductor extending from a second terminal of the RFID inlay;
   an RFID reader subsystem having a processor and an array of two or more spatially distributed antennas, each member of the antenna array being adapted to radiate and receive electromagnetic energy, the system adapted to:
      A) select a first of the antennas as a send antenna and second of the antennas as a receive antenna;
      B) select a desired transmit power and a desired transmit frequency;
      C) command transmission of energy from the send antenna at the desired transmit power and at the desired transmit frequency;
      D) monitor the receive antenna for a return signal resulting from the transmission of energy, the return signal having an information content which includes a moisture status indicator which indicates whether or not liquid is present on the pad;
      E) communicate a WET or DRY status to a destination, the WET or DRY status depending on the moisture status indicator;
      F) deselect the first antenna and select an antenna other than the just-deselected first antenna as the send antenna;
      G) deselect the second antenna and select an antenna other than the just-deselected second antenna as the receive antenna;
      H) deselect the transmit power and select a power other than the just-deselected transmit power as the desired transmit power;
      I) deselect the transmit frequency and select a frequency other than the just-deselected transmit frequency as the desired transmit frequency; and
      J) repeat C through J, wherein the second antenna and the first antenna are not the same antenna.

16. The system of claim 15 wherein the send antenna, the receive antenna, the desired transmit power, and the desired transmit frequency are each selected, in order, from respective lists of send antennas, receive antennas, desired transmit powers, and desired transmit frequencies.

17. The system of claim 15 wherein the send and receive antennas are selected as a pair, in order, from a list of send/receive antennas, the desired transmit power is selected, in order, from a list of desired transmit powers and the desired transmit frequency is selected, in order, from a list of desired transmit frequencies.

18. A system for detecting an incontinence event comprising:
   a pad which is deployable on a mattress and which, as deployed, has an open circuit comprised of a first conductor extending from a first terminal of an RFID inlay, and a second conductor extending from a second terminal of the RFID inlay;
   an RFID reader subsystem having a processor and an array of two or more spatially distributed antennas, each member of the antenna array being adapted to radiate and receive electromagnetic energy, the system adapted to:
      A) select a first of the antennas as a send antenna and second of the antennas as a receive antenna;
      B) select a desired transmit power and a desired transmit frequency;
      C) command transmission of energy from the send antenna at the desired transmit power and at the desired transmit frequency;
      D) monitor the receive antenna for a return signal resulting from the transmission of energy, the return signal having an information content which includes a moisture status indicator which indicates whether or not liquid is present on the pad;
      E) communicate a WET or DRY status to a destination, the WET or DRY status depending on the moisture status indicator;
      F) deselect the first antenna and select an antenna other than the just-deselected first antenna as the send antenna;
      G) deselect the second antenna and select an antenna other than the just-deselected second antenna as the receive antenna;
      H) deselect the transmit power and select a power other than the just-deselected transmit power as the desired transmit power;
      I) deselect the transmit frequency and select a frequency other than the just-deselected transmit frequency as the desired transmit frequency; and
      J) repeat C through J;
   wherein the send and receive antennas are selected as a pair, in order, from a list of send/receive antennas, the desired transmit power is selected, in order, from a list of desired transmit powers and the desired transmit frequency is selected, in order, from a list of desired transmit frequencies;
   wherein each list has a first member and a last member;
   wherein no member of the list of desired transmit powers has a magnitude which is a repetition of the magnitude of the immediately preceding member of the list of desired transmit powers; and
   wherein no member of the list of desired transmit frequencies has a magnitude which is a repetition of the magnitude of the immediately preceding member of the list of desired transmit frequencies.

19. The system of claim 18 wherein the last member of each list is treated as immediately preceding the first member of the list.

* * * * *